United States Patent [19]

Osikowicz et al.

[11] Patent Number: 5,075,078

[45] Date of Patent: Dec. 24, 1991

[54] SELF-PERFORMING IMMUNOCHROMATOGRAPHIC DEVICE

[75] Inventors: Eugene W. Osikowicz, Lake Zurich; Michael Beggs, Waukegan; Paul Brookhart, Gurnee; Russell B. Richerson, Lake Zurich; Frank Walsworth, Gurnee, all of Ill.

[73] Assignee: Abbott Laboratories, Abbott Park, Ill.

[21] Appl. No.: 417,346

[22] Filed: Oct. 5, 1989

[51] Int. Cl.⁵ .................. G01N 31/22; G01N 30/90; G01N 21/77

[52] U.S. Cl. ............................... 422/56; 436/162; 436/169

[58] Field of Search .............. 422/56; 436/162, 169, 436/530

[56] References Cited

U.S. PATENT DOCUMENTS

| | | | |
|---|---|---|---|
| 3,443,903 | 10/1965 | Haack et al. | 436/169 |
| 4,059,407 | 11/1977 | Hochstrasser | 422/56 |
| 4,094,647 | 6/1978 | Deutsch et al. | 422/56 |
| 4,168,146 | 9/1979 | Grubb et al. | 436/527 |
| 4,235,601 | 11/1980 | Deutsch et al. | 436/44 |
| 4,275,149 | 6/1981 | Litman et al. | 435/7 |
| 4,313,734 | 2/1982 | Leuvering | 436/525 |
| 4,361,537 | 11/1982 | Deutsch et al. | 422/56 |
| 4,366,241 | 12/1982 | Tom et al. | 435/7 |
| 4,373,932 | 2/1983 | Gribnau et al. | 436/501 |
| 4,435,504 | 3/1984 | Zuk et al. | 435/7 |
| 4,477,575 | 10/1984 | Vogel et al. | 436/170 |
| 4,689,309 | 7/1987 | Jones | 436/95 |
| 4,740,468 | 4/1988 | Weng et al. | 435/7 |
| 4,756,828 | 7/1988 | Litman et al. | 435/7 |
| 4,879,215 | 11/1989 | Weng et al. | 435/7 |
| 4,916,056 | 4/1990 | Brown, III et al. | 435/7 |
| 4,954,452 | 9/1990 | Yost et al. | 436/524 |
| 4,956,302 | 9/1990 | Gordon et al. | 436/161 |
| 4,960,691 | 10/1990 | Gordon et al. | 435/6 |

FOREIGN PATENT DOCUMENTS

| | | | |
|---|---|---|---|
| 0217403 | 8/1987 | European Pat. Off. | |
| 1109636 | 6/1983 | U.S.S.R. | 436/162 |
| 2204398 | 11/1988 | United Kingdom | 422/58 |

Primary Examiner—Robert J. Warden
Assistant Examiner—Arlen Soderquist
Attorney, Agent, or Firm—Daniel R. Curry

[57] ABSTRACT

Improved chromatographic strip binding assay devices are provided for determining the presence or amount of an analyte present in a patient sample. Assay label reagents interact with capture reagents immobilized in a testing region on the strip substrate to generate a visually detectable image indicative of the test result. The test result images include a minus sign (−) to indicate a negative test result for analyte which image is generated if the suspect analyte is absent in the patient sample and a plus sign (+) to indicate a positive test result for analyte which image is generated if the suspect analyte is present or is present at a pre-determined concentration in the patient sample. The immobilized capture reagents responsible for the location and configuration of the test result images are applied to the strip at an angled orientation with respect to the fluid flow direction of the strip to ensure that sharp substantially complete test result images are formed during performance of the assay. The devices provide substantially self-performing assays having inherently clear test results which are not subject to misinterpretation by the skilled or untrained user.

18 Claims, 5 Drawing Sheets

SELF-PERFORMING IMMUNOCHROMATOGRAPHIC DEVICE

The present invention relates to qualitative diagnostic test strip devices incorporating a visually detectable result format which generates or develops the image of a plus sign (+) to indicate a positive test result for analyte and a minus sign (−) to indicate a negative test result for analyte. More particularly, it relates to improved diagnostic test strip devices wherein the reagents responsible for the development of the test result image are angularly oriented with respect to the direction of fluid flow to provide a more complete and sharper image for the test result which is inherently clear and unmistakable.

In the development of the medical diagnostics field, there has been explosive growth in the number of substances to be detected in physiological test samples. Various analytical procedures are commonly used in diagnostic assays to determine the presence and/or amount of these substances of interest or clinical significance. These clinically significant or interesting substances are commonly referred to as analytes. Diagnostic assays have become an indispensable means for detecting analytes in test samples, and for the most part the medical profession has used highly automated clinical laboratories and sophisticated equipment for these determinations.

There is, however, an expanding need for having analytical capabilities in doctors' offices and in the home. Together with the diagnosis of disease or physiological conditions or disorders, there is a growing need to monitor the effects of drug therapy and chronic illness, to detect the use of drugs of abuse and to detect the presence of contaminants.

Numerous approaches have been developed toward this end, depending to varying degrees on instrumental or visual observation of the assay result. Typical of these methods are the so called "dipstick" and "flow-through" devices and methods. The dipstick generally uses a plastic strip with a reagent-containing matrix layered thereon. A test sample is applied to the device, and the presence of the analyte is indicated by a visually detectable signal such as a color-forming reaction. The flow-through device generally uses a porous material with a reagent containing matrix layered thereon or incorporated therein. Test sample is applied to and flows through the porous material, and analyte in the sample reacts with the reagent(s) to produce a detectable signal on the porous material.

Although, such devices have proven useful for the qualitative determination of the presence of analytes, they often require a number of manipulative steps, for example, the addition and incubation of assay reagents and the need for intermediate washing steps. These complex devices and methods are time consuming and require the close attention of a user who, depending on the device, must time the various assay steps and in some cases measure the reagents to be added.

Hochstrasser (U.S. Pat. No. 4,059,407) discloses a dipstick device which can be immersed in a biological fluid to semi quantitate analyte in the fluid. Semi quantitation of the analyte is accomplished by using a series of reagent containing pads wherein each pad in the series will produce a detectable color (i.e., a positive result) in the presence of an increasing amount of analyte. Also of interest in the area of dipstick devices are U.S. Pat. Nos. 3,802,842, 3,915,639 and 4,689,309.

Deutsch et al. describe a quantitative chromatographic test strip device in U.S. Pat. Nos. 4,094,647, 4,235,601 and 4,361,537. The device comprises a material capable of transporting a solution by capillary action, i.e., wicking. Different areas or zones in the strip contain the reagents needed to produce a detectable signal as the analyte is transported to or through such zones. The device is suited for both chemical assays and binding assays which are typified by the binding reaction between an antigen and its complementary antibody.

Many variations on the Deutsch et al. device have been disclosed. For example, Tom et al. (U.S. Pat. No. 4,366,241) disclose a bibulous strip with an immunosorbing zone to which the test sample is applied. Grubb et al. (U.S. Pat. No. 4,168,146) describe the use of a porous test strip material to which is covalently bound an antigen specific antibody. In performance of an assay, the test strip is immersed in a solution suspected of containing an antigen, and capillary migration of the solution up the test strip is allowed to occur. As the antigen moves up the test strip it binds to the immobilized antigen specific antibody. The presence of antigen is then determined by wetting the strip with a second antigen specific antibody to which a fluorescent or enzyme label is covalently bound. Quantitative testing can be achieved by measuring the length of the strip that contains bound antigen.

Weng et al. in U.S. Pat. No. 4,740,468 describe a chromatographic strip test device including an absorbant strip having an end portion for contacting a test solution. A test region is spaced from the end portion and contains a spot of immobilized antibody specific for analyte, for example. The strip also includes an unbound label capture zone including immobilized analyte analog. In use, a test solution is prepared by mixing patient sample with a first specific binding pair member, for example, a labelled antibody conjugate for analyte. After incubation, the test solution contains analyte/antibody label complexes and labelled antibody conjugate which is unbound to sample analyte. The test solution is contacted to the end of the strip which causes the test solution to migrate up the strip towards the test region. As the fluid front traverses the label capture zone, any excess or unbound label in the test solution binds to the analyte-analog at this zone and is prevented from further migration along the strip. If analyte/antibody-label complexes are present in the test solution, these complexes will continue to migrate to the test region where they are immobilized into a sandwich complex by the immobilized antibody located in this zone. Thereafter, the end portion of the strip may be contacted with other signal-system reagents which migrate up the strip to the test region and react with the label present in the sandwich complexes to generate a detectible signal. The presence or absence of a signal at the test region indicates the presence or absence of analyte in the patient sample.

The Weng et al. test device has a number of shortcomings. The device and method require the end user to mix and incubate the test solution and to add the signal-system reagents and the test solution in the proper sequence. The device has no procedural controls built in which will verify to the end user that all of the reagents are functioning properly and that the proper steps have been followed to indicate a reliable result.

An improved diagnostic test strip device is described in copending U.S. application Ser. No. 135,810, filed Dec. 21, 1987, now abandoned, and continuation application Ser. No. 282,978, filed Dec. 14, 1988 and assigned to the same assignee as the present invention. As described in that application, an improved strip device includes a test region having a capture reagent, typically an antibody, specific for sample analyte located thereat. A conjugate pad is located adjacent the test strip at an upstream sample entry location. The conjugate pad includes labelled antibody and any other assay reagents which may be desirable or required. In accordance with the improved design, the end user simply adds an amount of the patient sample, for example a bodily fluid such as blood, serum or urine, to a sample entry port. The patient sample migrates through the conjugate pad liberating and mixing sample fluids with the other assay reagents provided in the conjugate pad. The combined fluids migrate to the chromatographic strip and are drawn through the testing zone whereupon a signal may be developed. The improved device is also provided with an end of test region including a pH indicator dye located at the downstream end of the test strip which changes color upon contact with the test fluids to indicate that the test is over and that no further waiting is needed to obtain the test result. This device is user friendly and no mixing and multiple addition steps are required.

Diagnostic test devices providing a visually-detectable result format which generates or develops the image of a plus sign, i.e. a + sign, to indicate a positive or yes result and a minus sign, i.e. a − sign, to indicate a negative or no result are also known. A flow-through test device of this type and a strip test device of this type are described in commonly-assigned copending U.S. application Ser. No. 831,013, filed Feb. 18, 1986 and U.S. Pat. No. 4,916,056, respectively. The positive (+)/negative (−) test result format has enjoyed enthusiastic customer response and wide commercial success.

Nevertheless, improvements in the positive (+)/negative (−) result format for test strip devices are desired. More particularly and referring now to FIGS. 1a and 1b, a prior art positive (+)/negative (−) test strip device is illustrated. The test strip includes a chromatographic strip substrate of absorbant material. The test strip is shown to have a fluid flow direction from left to right. A sample entry region of the strip is shown at the enlarged darkened region at the left hand end of each strip. A testing region, generally centrally located on the strip is designated as a circular area. In accordance with these prior art strip devices, a procedural control bar is located in the testing region by immobilizing analyte onto the strip in a generally rectangular configuration. The procedural control bar is oriented on the strip so that the length dimension of the bar or rectangle extends parallel to the direction of fluid flow on the strip. In addition to the procedural control bar, a patient test bar is also located in the testing region by immobilizing antibody specific for the analyte being tested for onto the strip in a generally rectangular configuration. The patient test bar is oriented on the strip so that its length dimension extends traverse to the direction of fluid flow and intersects the procedural control bar in a generally perpendicular manner.

In accordance with these prior art devices, a fluid patient sample is added to the strip at the left hand sample entry end of the strip. The sample fluids migrate along the strip in the fluid flow direction until the fluids enter the testing region. If analyte is present in the sample it will bind to the antibody on the patient bar and become immobilized. A label reagent comprising an antibody conjugated to a labelling substance is added to the sample entry end and permitted to migrate into the testing region. The label antibody will bind to the immobilized analyte on the patient bar to form a labelled sandwich complex and in addition will bind to the immobilized analyte provided on the procedural control bar. Thereafter, other signal producing reagents may be added to the sample entry region. Upon migration to the testing region, these reagents may react with immobilized label substance found at the testing region to produce a visually detectable signal. An illustrative labelling system of this type comprises an enzyme as the labelling substance and a chromogenic substrate as the other signal producing reagent. Alternatively, a direct visually detectable label, such as the selenium colloid conjugate labels described in commonly-assigned copending application, U.S. Ser. No. 072,459, filed July 13, 1987, may also be used. The label conjugate can be premixed with sample prior to addition to the strip or it can be added substantially simultaneously with the sample or it can be added after sample addition.

In any event, the label employed generates a visually detectable image in the testing region where it becomes bound. The label is intended to form a minus sign upon interaction with the procedural control bar to indicate a negative test result, i.e. no analyte present in the sample, as shown in FIG. 1a. If analyte is immobilized on the patient test bar, the label is intended to generate a signal perpendicular to the procedural control bar completing formation of a plus sign + to indicate a positive test result, i.e. analyte was present in the test sample, as shown in FIG. 1i b.

Experience with these positive (+)/negative (−) test devices of this type has revealed that sometimes interactions between the sample fluids and/or the labelling and signal fluids and the immobilized capture reagents provided in the procedural control and patient bars may be inconsistent. Solvent front effects may also contribute to the inconsistent results sometimes observed. The results sometimes cause an incomplete image of the minus sign or the plus sign to be developed in the testing region. One observed inconsistency referred to as a leading edge effect is illustrated in the test results shown in FIGS. 2a and 2b. As shown in FIG. 2a, the colored signal generated by the label appears as a concentrated spot at the upstream left hand end of the procedural control bar. This result is believed to be caused by a localized depletion of label conjugate at the upstream end of the bar leaving little or no label conjugate remaining for binding to the downstream portions of the bar. An incomplete and easily misunderstood image bearing little resemblance to a minus sign is obtained.

In the case of the positive test result shown in FIG. 2b, the image formed appears as a spot located at the leading edge of the procedural control bar spaced from a darkened line of signal along the upstream leading edge of the patient bar adjacent an ill-defined trailing shadow area. An indistinct image which does not resemble a plus sign results. This image can easily be misinterpreted as a minus sign.

Accordingly, a positive (+)/negative (−) test strip device capable of consistently providing a strong, fully defined test result image which is inherently clear, leaving no room for misinterpretation of results is still desirable or required.

SUMMARY OF THE INVENTION

Unexpectedly, it has now been discovered that leading edge effects and other shortcomings of the prior art devices may be overcome by orienting the procedural control bar and the patient test bar on the test strip with respect to the fluid flow direction through the test region so that the distance across the bars travelled by the sample or test fluids is minimized.

More particularly, in accordance with the present invention a new and improved chromatographic strip binding assay device for detecting the presence or amount of an analyte present in a patient sample is provided. The test strip device is of the type which develops a visually detectable plus sign (+) to indicate a positive test result for analyte or a visually detectable minus sign (−) to indicate a negative test result for analyte.

The test strip device includes a chromatographic strip substrate having a length and width capable of conveying fluids in a fluid flow direction generally parallel to the length of the strip. The strip includes a sample contact region whereat a fluid patient sample and other assay reagents may be contacted with said strip. The strip also includes a testing region disposed on said strip at a downstream location from the sample contact region. The testing region includes a patient test bar defined by a first capture reagent specific for the analyte being tested, immobilized on the strip testing region in a generally rectangular configuration. A procedural control bar defined by a second capture reagent specific for an assay label immobilized on the strip test region in a generally rectangular configuration is also provided in the testing region. The patient test bar and the procedural control bar intersect each other in a generally perpendicular manner in the testing region.

The improvement in the test result image formation comprises immobilizing each of the patient test and procedural control bars on said strip testing region in an angled orientation with respect to the fluid flow direction of said strip to minimize the distance travelled by an added fluid across both the patient test bar and procedural control bar. Preferably, each of the bars are set at a 45° angle with respect to the fluid flow direction and at 90° with respect to each other.

In a preferred embodiment, the chromatographic strip substrate comprises nitrocellulose. The first capture reagent defining the patient test bar comprises immobilized antibody specific for the sample analyte being determined. The second capture reagent defining the procedural control bar comprises immobilized analyte. In the preferred embodiment the test strip device includes a application pad adjacent the sample contact region of the strip and in fluid flow contact therewith. The application pad receives the test sample and includes a porous substrate and a diffusible label application pad to the chromatographic strip with the sample fluids. Preferably the label conjugate comprises an antibody conjugated to a selenium colloid label material.

In accordance with an alternate embodiment, the label conjugate comprises a monoclonal antibody from a first species specific for the analyte being tested, conjugated to a labeling substance. Moreover, the second capture reagent comprises an antibody from a second species which immunologically reacts with the monoclonal antibody of the first species.

The new and improved chromatographic test strip devices of this invention provide sharp clearly defined test result images which unequivocally indicate a positive or negative test result. The assays are virtually self performing requiring the user to simply add a few drops of sample fluid to the sample entry region and wait a few minutes for an easily understood test result to be obtained. Rapid accurate and relatively inexpensive immunodiagnostic tests may be provided to physicians offices or to patients directly in this format.

Other objects and advantages will become apparent from the following detailed description taken in conjunction with the drawings in which:

DETAILED DESCRIPTION OF THE PREFERRED EMBODIMENT

Figure 3:
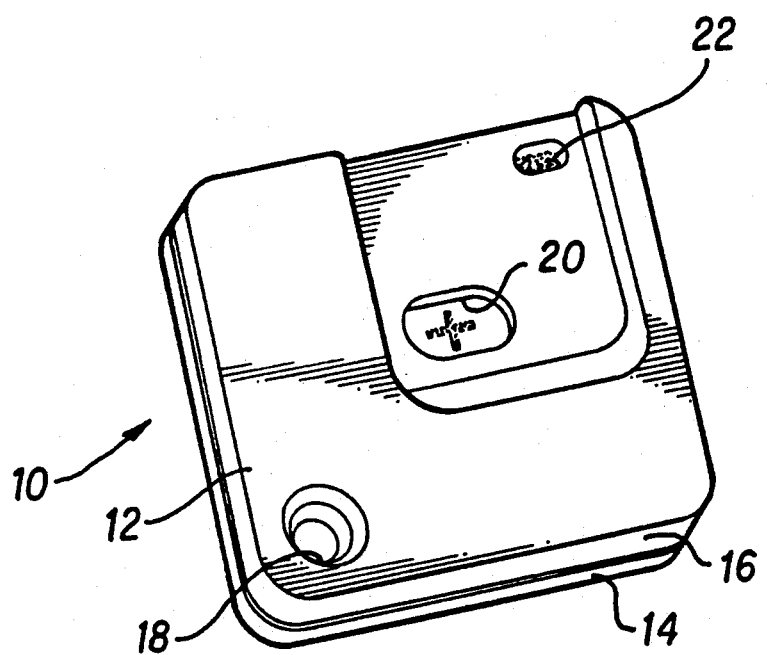
FIG. 3 is a perspective view of the new and improved chromatographic strip binding assay device of the present invention.

Referring now to FIG. 3, the new and improved chromatographic strip binding assay device 10 of the present invention is shown. Device 10 includes a two piece housing 12 including a lower half 14 and upper half 16. Housing lower half 14 and upper half 16 may be molded from any suitable thermoplastic molding material. Upper housing half 16 is provided with a sample fluid entry aperture 18 which is preferably provided with a flared entry as shown. A generally oval shaped test result viewing window 20 is defined in a central portion of top half 16. In the preferred embodiment shown in FIG. 3, upper half 16 also includes an end of test indicator window 22.

Figure 4:
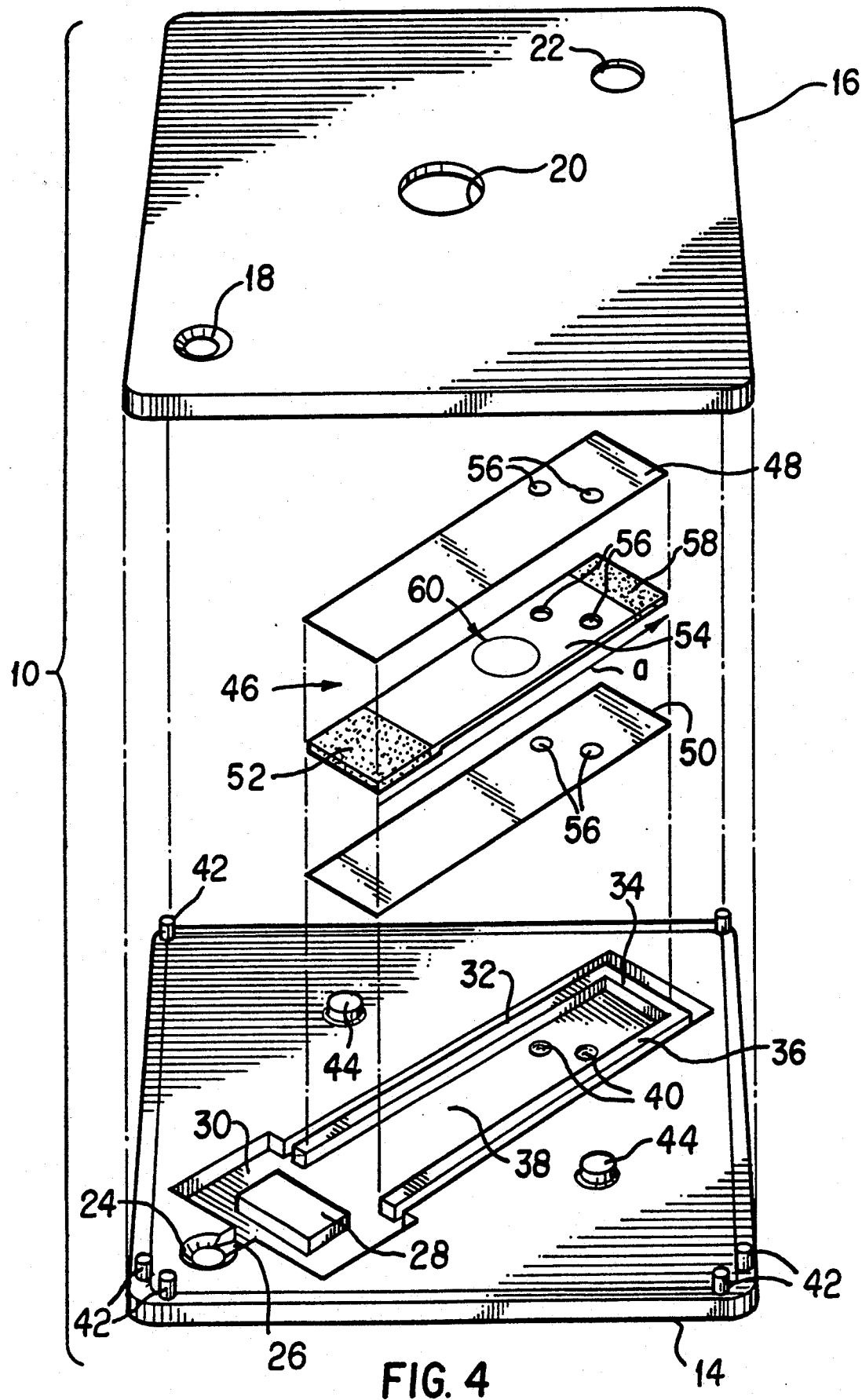
FIG. 4 is an exploded perspective view of the new and improved chromatographic strip binding assay device of the present invention.

Referring now to FIG. 4, an exploded perspective view of test device 10 is shown. Lower housing half 14 has an inwardly facing surface which is molded to provide a number of structural features. More particularly, a sample receiving bowl or well 24 is provided in lower half 14 aligned with sample fluid entry aperture 18 which receives droplets of a patient sample fluid. A downwardly angled trough exit 26 extends inwardly from sample receiving bowl 24 which introduces sample fluids to an edge portion of application pad 52 on strip substrate 46. Bottom housing half 14 includes a generally rectangular upstanding mesa support 28 spaced from trough exit 26 to support the application pad portion 52 of strip substrate 46. An enlarged rectangular recess 30 surrounds mesa support 28 for catching overflow of excess sample fluids. A series of upstanding sidewalls 32, 34 and 36 are provided to define a generally rectangular strip receiving recess 38. A pair of staggered depressions 40 are provided within recess 38 which are adapted to receive the ends of strip, not shown, positioning pins extending downwardly from top half 16 to further maintain the strip substrate 46 in a fixed position within housing 12. A pair of upwardly projecting pin receiving socket projections 44 are provided as well as a plurality of peripheral upwardly projecting pins 42 which are adapted to mate with complementary structures in upper housing half 16 to provide snap-fit engagement for securing the upper and lower housing halves together.

In the preferred embodiment shown in FIG. 4 the strip substrate 46 comprises a laminated assembly including a strip portion 54 having an application pad 52 bonded to one end and upper and lower plastic film layers 48 and 50, respectively. Plastic film layers 48 and 50 are provided to control evaporation of sample fluids, to prevent accidental contact with immobilized assay reagents disposed on strip 54 and to further promote a generally uniform linear fluid flow along strip 54. A pair of staggered apertures 56 pass through strip substrate 46 which are adapted to receive the above-mentioned strip positioning pins extending downwardly from upper housing half 16. As shown in FIG. 4, fluids are wicked or permitted to migrate along strip 54 parallel to the length of the strip in the direction shown by arrow, a. In the preferred embodiment, the downstream end of strip 54 has a pH indicator dye 58 coated or deposited thereon. The pH indicator dye 58 changes color when contacted by migrating sample and testing fluids which is observable through window 22. The testing region 60 is indicated as a phantom circular area at a centrally located portion on strip 54.

Figure 5:
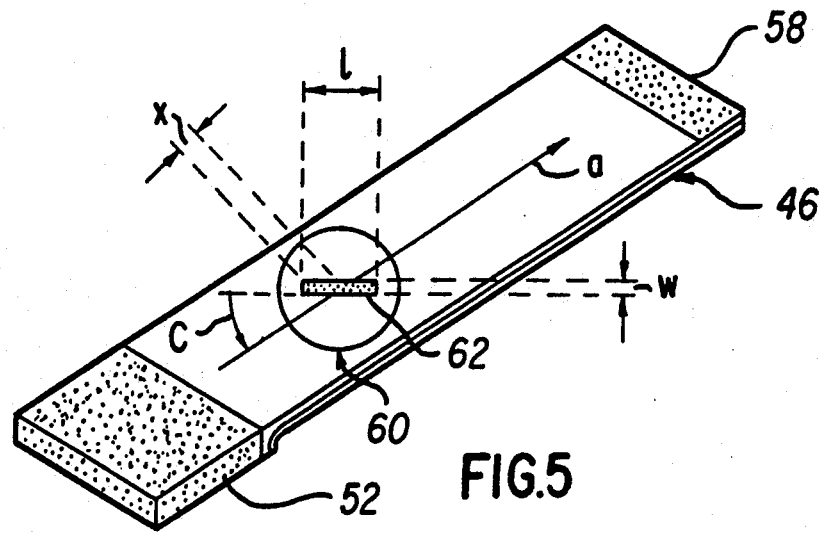
FIG. 5 is a perspective view of the new and improved strip substrate of the present invention illustrating a negative test result.
Figure 6:
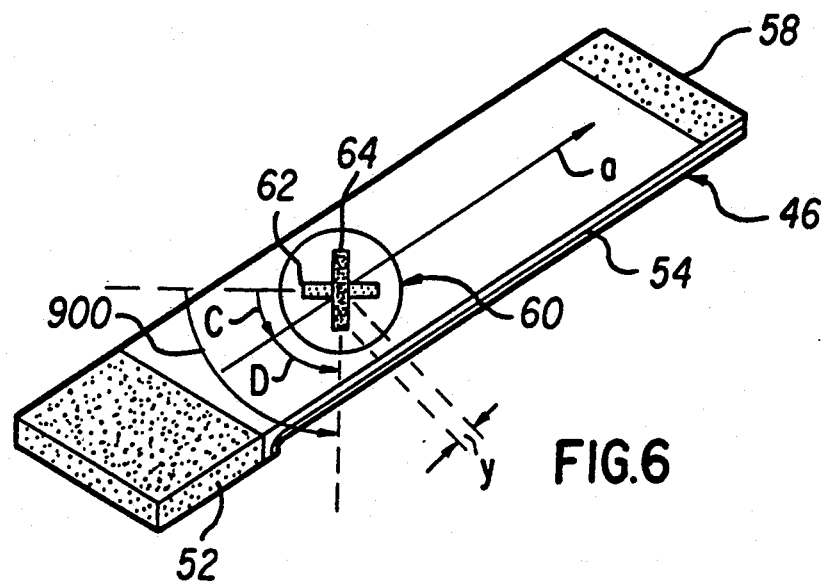
FIG. 6 is a perspective view of the new and improved strip substrate of the present invention illustrating a positive test result.

The testing region 60 of the new and improved chromatographic strip binding assay of the present invention is shown in greater detail in FIGS. 5 and 6. As shown in FIG. 5, a procedural control bar 62 is defined in testing region 60 by immobilizing a capture reagent specific for assay label on strip 54 in a generally rectangular bar configuration. The procedural control bar 62 is defined by a bar of immobilized capture reagent which is set at an angled orientation with respect to fluid flow direction, a, indicated as angle C.

Referring now to FIG. 6, testing region 60 also includes a patient test bar 64 defined by immobilizing a capture reagent specific for sample analyte on strip 54 in a generally rectangular bar configuration. The patient test bar 64 is defined by a bar of immobilized capture reagent which is set at an angled orientation with respect to the fluid flow direction, a, indicated as angle D.

The distance travelled by an added migrating fluid across procedural control bar 62 is shown as dimension X in FIG. 5. The distance travelled by a migrating fluid across patient test bar 64 is shown as dimension, Y, in FIG. 6.

In accordance with the present invention, the angular orientations of the procedural control bar and patient test bars defined by angles C and D are selected so that the total distance travelled by an added migrating fluid across both bars, represented by the sum of X+Y is minimized.

Angles C and D are generally complementary angles which may vary between 30° and 60° respectively. It is preferred that angles C and D are equal to each other at 45° to minimize the sum of X and Y dimensions.

The distance across the procedural control bar 62, indicated as dimension X, when angle C is approximately 90°. At C=90° for the procedural control bar, the corresponding dimension Y for the patient control bar 64 will be at maximum and angle D for the patient bar will be 0°. This corresponds to the devices shown in FIGS. 1 and 2 which were susceptible to leading edge effect imaging problems.

Figure 2A:
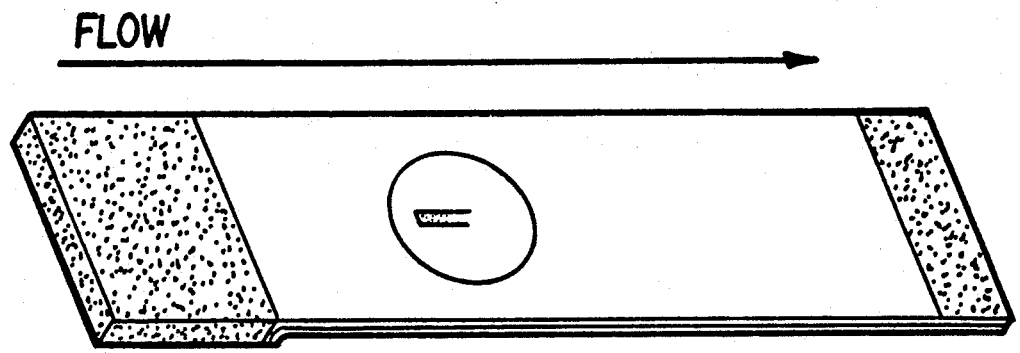
FIGS. 2a and 2b are perspective views of prior art chromatographic test strip devices illustrating incomplete test result image formation sometimes observed with these devices to illustrate leading edge effects.
Figure 2B:
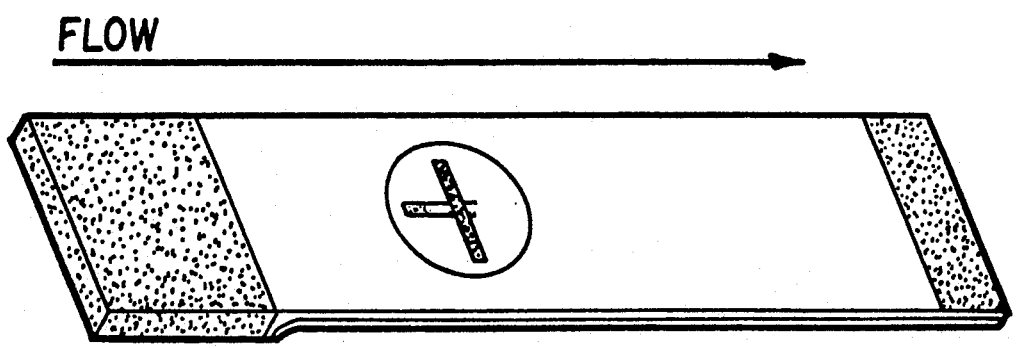

As shown in FIGS. 5-6, the distance X is also uniform along the entire length, l, of procedural control bar 62. When angle C equals 45°, X is only slightly greater than the width, w, of the procedural control bar 62. As a migrating fluid front containing an assay label conjugate moving in the direction of arrow, a, and extending across the entire width of the strip passes through the testing zone 60, portions of the fluid front contact the capture reagent present in the procedural control bar 62 at different times. This permits a test result image to be formed along the entire upstream edge of the procedural control bar 62. This avoids the spot formation which occurred with the prior art devices as shown in FIGS. 2a and 2b wherein the procedural control bar was parallel to flow direction a, i.e. wherein C=0°. Moreover, because the total distance (X+Y) across the bars is minimized, label conjugate in the fluid front binds more uniformly to the capture reagents across the entire distance X and distance Y without the localized conjugate depletion previously observed. This results in a substantially complete, sharp and well-defined rectangular bar image being developed by immobilizing the assay label substantially uniformly within the entire procedural control bar area and the patient control bar area as shown in FIGS. 5 and 6.

By way of further illustration, the new and improved test device of this invention may comprise a test for early detection of human pregnancy. In this case, the test device performs an immunoassay for detecting an elevated level of human chorionic gonadotropin (hCG), a hormone which is present in patient urine samples at elevated levels during early stages of pregnancy. In accordance with this format, the device of this invention includes a patient test bar defined by an immobilized anti-Beta HCG antibody. The label conjugate employed comprises for example an anti-Beta HCG antibody conjugated to a selenium colloid label. The procedural control bar may comprise a immobilized hCG/anti-Beta hCG complex. In accordance with the method of use, a doctor or a patient adds a few drops of patient urine sample into the sample fluid entry aperture. The patient specimen wets the application pad, and the selenium colloid conjugate in the pad migrates with the sample fluid along the strip and through the testing region. If the patient specimen does not contain hCG the reddish-pink colored selenium conjugate binds only to the procedural control bar of the test region which forms the image of a minus sign (−) in the test result viewing window. This clearly and unequivocally indicates that no hCG is present in the sample and that the test is functioning properly.

If hCG is present in the patient sample, patient hCG binds to the anti-hCG antibody on the label conjugate to form a labelled analyte complex which then binds to the anti-hCG antibody in the patient test bar forming a reddish-pink bar intersecting the procedural control bar, thereby forming the image of the plus sign (+) in the test result viewing window. The plus sign clearly and unequivocally indicates that the patient is pregnant.

The patient or physician can obtain a reliable diagnosis of whether the patient is pregnant or not in less than five minutes.

Referring again to FIG. 6, in the test device 10 in accordance with the present invention, the intersecting procedural control bar 62 and patient test bar 64 by virtue of their angled orientation on the strip present a pair of upstream arms and a pair of downstream arms to a migrating fluid front moving along the strip in direction, a. It may be possible that the interaction between the label conjugate and the upstream arm portions of the bars 62 and 64 may significantly reduce the amount of label conjugate available for binding to the downstream arm portions disposed on the same side of strip, leading to what is referred to as a shadow effect.

Figure 7:
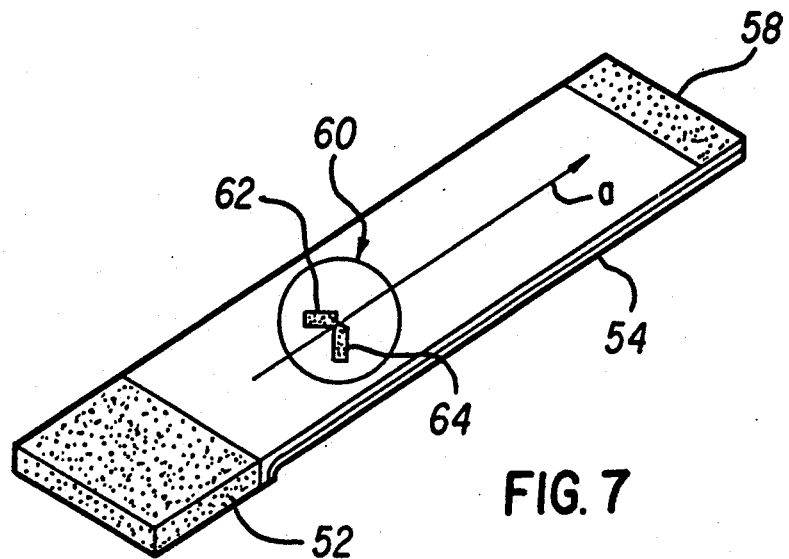
FIG. 7 is a perspective view of a strip substrate illustrating a potential shadow in effect problem which is avoided by alternate embodiment of this invention.

The shadow effect is illustrated more clearly in FIG. 7, wherein instead of developing a complete positive plus sign (+) image in the testing region 60, an incomplete sideways V-shaped image results. The shadow effect may be remedied by decreasing the concentration of capture reagents present in the procedural control bar and the patient test bar and increasing the amount of label conjugate. Generally these steps are sufficient to restore or provide the complete, well defined plus sign (+) image.

In accordance with an alternate embodiment of this invention, the label conjugate comprises a monoclonal antibody from a first species conjugated to the labelling substance. The procedural control bar no longer includes an immobilized analyte but instead includes an immobilized antibody from a second species which is specific for the monoclonal antibody in the label conjugate from the first species. In the hCG assay example, the label conjugate may comprise a mouse monoclonal anti hCG selenium conjugate. The procedural control bar capture reagent may comprise a specific anti mouse IgG antibody immobilized to the strip. In this alternate embodiment the development of a minus sign (−) at the procedural control bar indicates that the mouse anti hCG selenium conjugate has migrated past the procedural control bar and been bound by the anti-mouse capture reagent.

Having described the structural details of the new and improved assay device of this invention, the discussion will turn to a description of the materials and methods for making and using the device of this invention.

In use of an assay device according to the invention, a test sample, which can be a liquid which is used directly as obtained from the source, or which has been pretreated in a variety of ways so as to modify its character, is introduced to the device through the application pad. The sample passes through the application pad, where it contacts one or more reagents involved in producing the assay reaction, to the chromatographic material through which the test sample will wick and in which it will encounter one or more additional reagents involved in producing the detectable signal.

Virtually any liquid sample can be used, so long as the sample has a reasonable rate of passage through the application pad and a reasonable rate of transport along the chromatographic material. The test sample can be derived from any desired source, such as a physiological fluid, for example, blood, saliva, ocular lens fluid, cerebral spinal fluid, sweat, urine, milk, ascites fluid, mucous, synovial fluid, peritoneal fluid, amniotic fluid or the like. The fluid can be pretreated prior to use, such as preparing plasma from blood, diluting viscous fluids, or the like; methods of treatment can also involve separation, filtration, distillation, concentration, inactivation of interfering components, and the addition of reagents. Besides physiological fluids, other liquid samples such as water, food products and the like can be used. In addition, a solid can be used once it is modified to form a liquid medium.

The present invention is particularly advantageous in that it combines several elements to form a novel assay device with which a one-step assay can be performed. The novel device simplifies the assay protocols by decreasing the number of manual steps required for its use, thereby reducing the risk of errors during use. The combination of elements in the present invention also enables the use of predetermined amounts of reagents incorporated within the device, thereby avoiding the need for reagent measurements and additions by the user. Furthermore, the reagents are situated in the device in such a way as to make the assay substantially self-performing and to facilitate the detection and quantitation of the assay results.

Definitions

A "specific binding member", as used herein, is a member of a specific binding pair, i.e., two different molecules wherein one of the molecules through chemical or physical means specifically binds to the second molecule. In addition to antigen and antibody specific binding pairs, other specific binding pairs include, as examples without limitation, biotin and avidin, carbohydrates and lectins, complementary nucleotide sequences such as the probe and capture nucleic acids used in hybridization reactions with a target nucleic acid sequence as the analyte, complementary peptide sequences, effector and receptor molecules, enzyme cofactors and enzymes, enzyme inhibitors and enzymes, enzyme substrates and enzymes, a peptide sequence and an antibody specific for the sequence or the entire protein, and the like. Furthermore, specific binding pairs can include members that are analogs of the original specific binding member, for example an analyte-analog. If the specific binding member is an immunoreactant it can be, for example, an antibody, antigen, hapten, or complex thereof, and if an antibody is used, it can be a monoclonal or polyclonal antibody, a recombinant protein or antibody, a mixture(s) or fragment(s) thereof, as well as a mixture of an antibody and other specific binding members. The details of the preparation of such antibodies and their suitability for use as specific binding members are well known to those skilled in the art.

When an immunoreactive specific binding member is attached to the chromatographic material of the present invention, the device is referred to as an "immunochromatograph", and the corresponding method of analysis is referred to as "immunochromatography". Immunochromatography, as used herein, encompasses both sandwich and competitive immunoassay techniques.

An "analyte", as used herein, is the compound or composition to be detected or measured in the test sample. In a binding assay, the analyte will have at least one epitope or binding site for which there exists a naturally occurring, complementary specific binding member or for which a specific binding member can be prepared. "Analyte" also includes any antigenic substances, haptens, antibodies, and combinations thereof. The analyte of interest in an assay can be, for example, a protein, a peptide, an amino acid, a nucleic acid, a hormone, a steroid, a vitamin, a pathogenic microorganism for which polyclonal and/or monoclonal antibodies can be produced, a natural or synthetic chemical substance, a contaminant, a drug including those administered for therapeutic purposes as well as those administered for illicit purposes, and metabolites of or antibodies to any of the above substances.

Examples of the hormones which are suitable as analytes for this invention are the following: thyroid stimulating hormone (TSH), human chorionic gonadotropin (hCG), luteinizing hormone (LH) and follicle stimulating hormone (FSH). An especially preferred hormone analyte in pregnancy testing is hCG.

Pathogenic microorganisms suitable for analysis by the present invention include those microorganisms disclosed in U.S. Pat. No. 4,366,241, which is herein incorporated by reference. Illustrative of some of these microorganisms are those associated with urinary tract infections, such as *Streptococcus pyogenes, Streptococcus salivarus, Escheria coli, Staphylococcus aureus, Klebsiella pneumonia, Proteus mirabilis* and the like. The microorganisms, when assayed by the present invention, may be intact, lysed, ground or otherwise fragmented and the resulting composition or portion thereof assayed. Preferably, the microorganisms are assayed intact.

The term "analyte-analog", as used herein, refers to a substance which cross-reacts with an analyte-specific binding member, although it may do so to a greater or a lesser extent than does the analyte itself. The analyte-analog can include a modified analyte as well as a fragmented or synthetic portion of the analyte molecule so long as the analyte-analog has at least one epitopic site in common with the analyte of interest.

"Label", as used herein, is any substance which is attached to a specific binding member and which is capable of producing a signal that is detectable by visual or instrumental means. Various suitable labels for use in the present invention can include chromogens, catalysts, fluorescent compounds, chemiluminescent compounds, radioactive labels, direct visual labels including colloidal metallic and non-metallic particles, dye particles, enzymes or substrates, or organic polymer latex particles, liposomes or other vesicles containing signal producing substances, and the like.

A large number of enzymes suitable for use as labels are disclosed in U.S. Pat. No. 4,275,149, columns 19-23, herein incorporated by reference. A particularly preferred enzyme/substrate signal producing system useful in the present invention is the enzyme alkaline phosphatase wherein the substrate used is nitro blue tetrazolium 5-bromo-4-chloro-3-indolyl phosphate or a derivative or analog thereof.

In an alternative signal producing system, the label can be a fluorescent compound where no enzymatic manipulation of the label is required to produce a detectable signal. Fluorescent molecules such as fluorescein, phycobiliprotein, rhodamine and their derivatives and analogs are suitable for use as labels in this reaction.

In an especially preferred embodiment, a visually detectable, colored particle can be used as the label component of the indicator reagent, thereby providing for a direct colored readout of the presence of concentration of the analyte in the sample without the need for further signal producing reagents. Materials for use as the colored particles are colloidal metals, such as gold, and dye particles as disclosed in U.S. Pat. Nos. 4,313,734 and 4,373,932. The preparation and use of non-metallic colloids, such as colloidal selenium particles, are disclosed in co-owned U.S. Pat. No. 4,954,452.

The use of colloidal particle labels in immunochromatography is disclosed in co-owned and copending U.S. patent application Ser. No. 072,459, filed July 13, 1987. Organic polymer latex particles for use as labels are disclosed in co-owned and copending U.S. patent application Ser. No. 248,858, filed Sept. 23, 1988.

A "signal producing component", as used herein, refers to any substance capable of reacting with another assay reagent or the analyte to produce a reaction product or signal that indicates the presence of the analyte and that is detectable by visual or instrumental means. "Signal production system", as used herein, refers to the group of assay reagents that are needed to produce the desired reaction product or signal. For example, one or more signal producing components can be used to react with a label and generate the detectable signal, i.e., when the label is an enzyme, amplification of the detectable signal is obtained by reacting the enzyme with one or more substrates or additional enzymes to produce a detectable reaction product.

An "ancillary specific binding member", as used herein, refers to any member of a specific binding pair which is used in the assay in addition to the specific binding members of the capture reagent and the indicator reagent and which becomes a part of the final binding complex. One or more ancillary specific binding members can be used in an assay. For example, an ancillary specific binding member can be capable of binding the analyte, as well as a second specific binding member to which the analyte itself could not attach.

Reagents and Materials

A. Binding Assay Reagents

In the present invention, binding assays involve the specific binding of the analyte and/or an indicator reagent (comprising a label attached to a specific binding member) to a capture reagent (comprising a second specific binding member) which immobilizes the analyte and/or indicator reagent on a chromatographic material or which at least slows the migration of the analyte or indicator reagent through the chromatographic material.

The label, as described above, enables the indicator reagent to produce a detectable signal that is related to the amount of analyte in the test sample. The specific binding member component of the indicator reagent enables the indirect binding of the label to the analyte, to an ancillary specific binding member or to the capture reagent. The selection of a particular label is not critical, but the label will be capable of generating a detectable signal either by itself, such as a visually detectable signal generated by colored organic polymer latex particles, or in conjunction with one or more additional signal producing components, such as an enzyme/substrate signal producing system. A variety of different indicator reagents can be formed by varying either the label or the specific binding member, it will be appreciated by one skilled in the art that the choice involves consideration of the analyte to be detected and the desired means of detection.

The capture reagent, in a binding assay, is used to facilitate the observation of the detectable signal of substantially separating the analyte and/or the indicator reagent from other assay reagents and the remaining components of the test sample. The capture reagent of the present invention is a specific binding member, such as those described above. In a binding assay, the capture reagent is immobilized on the chromatographic material to form a "capture situs", i.e., that region of the chromatographic material having one or more capture reagents non-diffusively attached thereto.

B. Application Pad

The application pad is in fluid flow contact with one end of the chromatographic material, referred to as the proximal end, such that the test sample can pass or migrate from the application pad to the chromatographic material; fluid flow contact can include physical contact of the application pad to the chromatographic material as well as the separation of the pad from the chromatographic strip by an intervening space or additional material which still allows fluid flow between the pad and the strip. Substantially all of the application pad can overlap the chromatographic material to enable the test sample to pass through substantially any part of the application pad to the proximal end of the strip of chromatographic material. Alternatively, only a portion of the application pad might be in fluid flow contact with the chromatographic material. The application pad can be any material which can transfer the test sample to the chromatographic material and which can absorb a volume of test sample that is equal to or greater than the total volume capacity of the chromatographic material.

Materials preferred for use in the application pad include nitrocellulose, porous polyethylene frit or pads and glass fiber filter paper. The material must also be chosen for its compatibility with the analyte and assay reagents, for example, glass fiber filter paper was found to be the preferred application pad material for use in a human chorionic gonadotropin (hCG) assay device.

In addition, the application pad contains one or more assay reagents either diffusively or non-diffusively attached thereto. Reagents which can be contained in the application pad include, but are not limited to, indicator reagents, ancillary specific binding members, and any signal producing system components needed to produce a detectable signal. For example, in a binding assay it is preferred that an indicator reagent be diffusively attached to the application pad; this eliminates the need to combine test sample and indicator reagent prior to use in an assay. The isolation of assay reagents in the application pad also keeps interactive reagents separate and facilitates the manufacturing process.

The application pad receives the test sample, and the wetting of the application pad by the sample will perform at least two functions. First, it will dissolve or reconstitute a predetermined amount of reagent contained by the pad. Secondly, it will initiate the transfer of both the test sample and the freshly dissolved reagent to the chromatographic material. In some instances, the application pad serves a third function as both an initial mixing site and a reaction site for the test sample and reagent.

In one preferred embodiment of the present invention, gelatin is used to encompass all or part of the application pad. Typically, such encapsulation is produced by overcoating the application pad with fish gelatin. The effect of this overcoating is to increase the stability of the reagent contained by the application pad. The application of test sample to the overcoated application pad causes the gelatin to dissolve and thereby enables the dissolution of the reagent. In an alternative embodiment of the present invention, the reagent containing application pad is dried or lyophilized to increase the shelf-life of the device. Lyophilized application pads were found to produce stronger signals than air dried application pads, and the lyophilized application pads maintained stability for longer periods. The reagents contained in the application pad are rehydrated with the addition of test sample to the pad.

In another preferred embodiment, the present invention can be further modified by the addition of a filtration means. The filtration means can be a separate material placed above the application pad or between the application pad and the chromatographic material, or the material of the application pad itself can be chosen for its filtration capabilities. The filtration means can include any filter or trapping device used to remove particles above a certain size from the test sample. For example, the filter means can be used to remove red blood cells from a sample of whole blood, such that plasma is the fluid received by the application pad and transferred to the chromatographic material. Such filter means are disclosed by U.S. Pat. No. 4,477,575 and WO Application No. 86/02192, published Apr. 23, 1987.

A still further preferred modification of the present invention involves the use of an additional layer or layers of porous material placed between the application pad and the chromatographic material or overlaying the application pad. Such an additional pad or layer can serve as a means to control the rate of flow of the test sample from the application pad to the chromatographic material. Such flow regulation is preferred when an extended incubation period is desired for the reaction of the test sample and the reagent(s) in the application pad. Alternatively, such a layer can contain an additional assay reagent(s) which is preferably isolated from the application pad reagents until the test sample is added, or it can serve to prevent unreacted assay reagents from passing to the chromatographic material.

When small quantities of non-aqueous or viscous test samples are applied to the application pad, it may be necessary to employ a wicking solution, preferably a buffered wicking solution, to carry the reagent(s) and test sample from the application pad and through the chromatographic material. When an aqueous test sample is used, a wicking solution generally is not necessary but can be used to improve flow characteristics or adjust the pH of the test sample. In immunochromatography, the wicking solution typically has a pH range from about 5.5 to about 10.5, and more preferably from about 6.5 to about 9.5. The pH is selected to maintain a significant level of binding affinity between the specific binding members in a binding assay. When the label component of the indicator reagent is an enzyme, however, the pH also must be selected to maintain significant enzyme activity for color development in enzymatic signal production systems. Illustrative buffers include phosphate, carbonate, barbital, diethylamine, tris, 2 -amino-2 -methyl-1 -ropanol and the like. The wicking solution and the test sample can be combined prior to contacting the application pad or they can be contacted to the application pad sequentially. Further detailed information relating to the application pads may be found in commonly assigned copending U.S. application Ser. No. 135,810, filed Dec. 21, 1987.

C. Chromatographic Material

The chromatographic material of the assay device of the present invention can be any suitably absorbant, porous or capillary possessing material through which a solution containing the analyte can be transported by a wicking action. Natural, synthetic, or naturally occurring materials that are synthetically modified, can be used as the chromatographic material including, but not limited to: cellulose materials such as paper, cellulose, and cellulose derivatives such as cellulose acetate and nitrocellulose; fiberglass; cloth, both naturally occurring (e.g., cotton) and synthetic (e.g., nylon); porous gels such as silica gel, agarose, dextran, and gelatin; porous fibrous matrixes; starch based materials, such as Sephadex ® brand cross-linked dextran chains; ceramic materials; films of polyvinyl chloride and combinations of polyvinyl chloride-silica; and the like. The chromatographic material should not interfere with the production of a detectable signal. The chromatographic material should have a reasonable inherent strength, or strength can be provided by means of a supplemental support.

A preferred chromatographic material is nitrocellulose. When nitrocellulose is used, however, the material of the application pad should be chosen for its ability to premix the test sample and the first reagent, i.e., fluid-flow through a nitrocellulose membrane is laminar and does not provide the more turbulent flow characteristics which allows the initial mixing of test sample and application pad reagents within the chromatographic material. If nitrocellulose is used as the chromatographic material, then Porex ® hydrophilic polyethylene frit or glass fiber filter paper are appropriate application pad materials because they enable the mixing and reaction of the test sample and application pad reagents within the application pad and before transfer to the chromatographic material. An especially preferred chromatographic material is glass fiber filter paper. Especially preferred for use as the chromatographic material are nitrocellulose laminated strips described in commonly assigned copending U.S. application Ser. Nos. 413,519; 413,569 and 413,571 filed concurrently of Sept. 27, 1989.

The particular dimensions of the chromatographic material will be a matter of convenience, depending upon the size of the test sample involved, the assay protocol, the means for detecting and measuring the signal, and the like. For example, the dimensions may be chosen to regulate the rate of fluid migration as well as the amount of test sample to be imbibed by the chromatographic material.

As discussed above, in a binding assay the patient test bar and procedural control bar can be formed by directly or indirectly attaching their respective capture reagent to the chromatographic material. Direct attachment methods include adsorption, absorption and covalent binding such as by use of (i) a cyanogen halide, e.g., cyanogen bromide or (ii) by use of glutaraldehyde. Depending on the assay, it may be preferred, however, to retain or immobilize the desired reagent on the chromatographic material indirectly through the use of insoluble microparticles to which the reagent has been attached. The means of attaching a reagent to the microparticles encompasses both covalent and non-covalent means, that is adhered, absorbed or adsorbed. It is preferred that capture reagents be attached to the microparticles by covalent means. By "retained and immobilized" is meant that the particles, once on the chromatographic material, are not capable of substantial movement to positions elsewhere within the material. The particles can be selected by one skilled in the art from any suitable type of particulate material composed of polystyrene, polymethylacrylate, polyacrylamide, polypropylene, latex, polytetrafluoroethylene, polyacrylonitrile, polycarbonate, glass or similar materials. The size of the particles is not critical, although generally it is preferred that the average diameter of the particles be smaller than the average pore or capillary size of the chromatographic material.

The capture reagent(s), signal producing component(s) or reagent coated microparticles can be deposited singly or in various combinations on or in the chromatographic material in a variety of configurations to produce different detection or measurement formats. For example, a reagent can be deposited as a discrete situs having an area substantially smaller than that of the entire chromatographic material.

It is also within the scope of this invention to have a reagent, at the downstream or distal end of the chromatographic material, which indicates the completion of a binding assay (i.e., end of assay indicator) by changing color upon contact with the test solution, wicking solution or a signal producing component. Reagents which would change color upon contact with a test solution containing water are the dehydrated transition metal salts, such as $CuSO_4$, $Co(NO_3)_2$, and the like. The pH indicator dyes can also be selected to respond to the pH of the buffered wicking solution. For example, phenolphthalein changes from clear to intense pink upon contact with a wicking solution having a pH range between 8.0-10.0, which is a common pH range for the assay fluids.

Reagents can be added directly to either the application pad or the chromatographic material during the performance of the assay. The preferred embodiment of the invention, however, involves the incorporation of all necessary assay reagents into the assay device so that only a liquid test sample need be contacted to the application pad to perform the assay. Therefore, one or more assay reagents can be present in either or both the application pad or chromatographic material of the present invention.

The present invention further provides kits for carrying out binding assays. For example, a kit according to the present invention can comprise the assay device with its incorporated reagents as well as a wicking solution and/or test sample pretreatment reagents as described above. Other assay components known to those skilled in the art, such as buffers, stabilizers, detergents, bacteria inhibiting agents and the like can also be present in the assay device and wicking solution.

In a sandwich binding assay, the migrating test solution or test sample contains both the dissolved indicator reagent from the application pad and the analyte from the test sample. Accordingly, both the indicator reagent and analyte are carried downstream by the advancing liquid front. Moreover, during their migration, the indicator reagent can bind to the analyte to form an indicator reagent/analyte complex. As the wicking liquid transports the indicator reagent/analyte complex through the chromatographic material, the immobilized capture reagent also binds to the analyte to render the indicator reagent/analyte complex immobilized. Thus, the indicator reagent/analyte complex is able to advance only as long as capture reagent binding sites on the chromatographic material are already occupied and no longer available for further binding. Consequently, the greater the concentration of analyte in the test sample, the further the distal migration of the indicator reagent/analyte complex through the chromatographic material even beyond the testing region.

Any further details needed regarding the materials, reagents and methods for making them are amply provided in the above-mentioned cited patent document or are generally known by those skilled in this art. Each of the above-cited patents and pending patent applications, in its entirety, is specifically incorporated herein by reference.

Although the present invention has been described with reference to certain preferred embodiments, modifications or changes may be made therein by those skilled in this art without departing from the scope or spirit of the present invention, as defined by the appended claims.

What is claimed is:

1. In a chromatographic strip binding assay device, for detecting the presence or amount of an analyte in a patient sample, wherein a visually detectable plus sign (+) develops to indicate a positive test result or a visually detectable minus sign (−) develops to indicate a negative test result, the device comprising:
   a chromatographic strip having a length and narrow width capable of conveying fluids in a fluid flow direction generally parallel to the length of said strip, said strip comprising
   a sample contact region whereat a fluid patient sample and other assay reagents may be contacted with said strip, and
   a testing region disposed on said strip at a downstream location from said sample contact region, said testing region comprising
   a patient test bar defined by a first capture reagent, specific for the analyte, immobilized on said strip in a generally rectangular configuration, and
   a procedural control bar defined by a second capture reagent, specific for an assay label, immobilized on said strip in a generally rectangular configuration, said patient test bar and said procedural control bar intersecting each other in a generally perpendicular manner;
   wherein the the testing region improvement comprises: said patient test bar and said procedural control bar each being immobilized on said strip in an angled orientation with respect to the fluid flow direction of said strip to minimize the distance travelled by an added migrating fluid across both said patient test bar and said procedural control bar.

2. A device as in claim 1, wherein the angular orientations of said patient test bar and said procedural control bar with respect to the fluid flow direction are defined by complementary angles varying between about 30° to about 60°, respectively.

3. A device as in claim 1, wherein the angled orientation of said patient test bar and said procedural control bar with respect to the fluid flow direction is about 45°, respectively.

4. A device as in claim 1, wherein said chromatographic strip substrate comprises nitrocellulose.

5. A device as in claim 1, wherein said first capture reagent comprises a specific binding pair member for analyte.

6. A device as in claim 5, wherein said first capture reagent is selected from the group comprising an antigen or an antibody.

7. A device as in claim 1, wherein said second capture reagent comprises a specific binding pair member for said assay label.

8. A device as in claim 7, wherein said second capture reagent is selected from the group comprising an antigen or an antibody.

9. A device as in claim 1, further comprising a housing for surrounding and holding said strip, said housing comprising: a sample entry aperture disposed adjacent said sample contact region of said strip, and a test result window disposed adjacent said testing region of said strip.

10. A device as in claim 1, further comprising a conjugate pad comprising a porous pad substrate, having said assay label therein, disposed adjacent said strip at said sample contact region.

11. A device as in claim 10, wherein said first capture reagent comprises an antibody specific for the analyte, said second capture reagent comprises immobilized analyte, and said assay label in said conjugate pad comprises an antibody, specific for the analyte, conjugated to a labelling substance.

12. A device as in claim 11, wherein said labelling substance is a selenium colloid label.

13. A device as in claim 11, wherein said second capture reagent comprises an immobilized antibody/analyte complex.

14. A device as in claim 10, wherein said first capture reagent comprises an antibody specific for the analyte, said second capture reagent comprises an antibody specific for said assay label, and said assay label comprises an antibody, specific for the analyte, conjugated to a labelling substance.

15. A device as in claim 14, wherein said labelling substance is a selenium colloid label.

16. A device as in claim 14, wherein said assay label comprises a monoclonal antibody from a first species specific for the analyte being tested for and said second capture reagent comprises an antibody from a second species specific for the monoclonal antibody of the first species.

17. A device as in claim 16, wherein said assay label comprises a mouse monoclonal antibody specific for the analyte, and said second capture reagent comprises an anti-mouse IgG antibody.

18. A device as in claim 1, further comprising an end of test indicator region on said strip at a downstream location from said testing region and defined by an indicator reagent capable of generating a visually detectable signal upon contact with testing fluids to indicate that fluids have flowed to said end of test indicator region and that the test result indicated at said testing region is a final test result.

* * * * *

UNITED STATES PATENT AND TRADEMARK OFFICE
CERTIFICATE OF CORRECTION

Figure 1A:
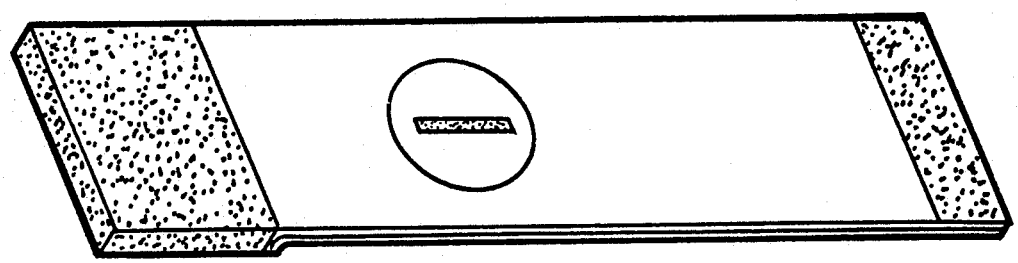
FIGS. 1a and 1b are perspective views of prior art chromatographic strip test devices illustrating a negative test result image and a positive test result image, respectively.
Figure 1B:
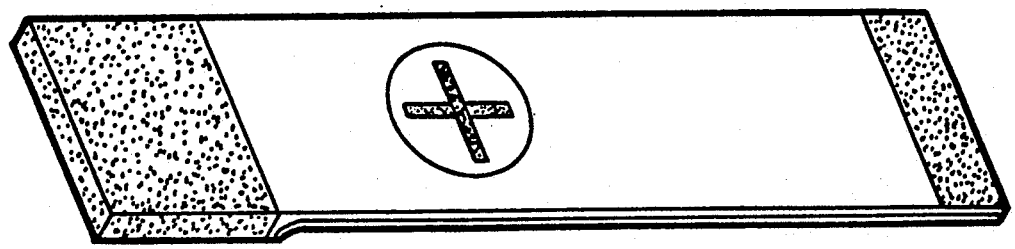

PATENT NO. : 5,075,078
DATED : December 24, 1991
INVENTOR(S) : E. Osikowicz; M. Beggs; P. Brookhart; R. Richerson; F. Walsworth It is certified that error appears in the above-identified patent and that said Letters Patent is hereby corrected as shown below:

Column 4, Line 35:

Change "FIG. 1i b" to --FIG. 1b--

Column 7, Lines 4-5:

Change "the ends of strip, not shown, positioning pins" to
        --the ends of strip positioning pins, not shown,--

Column 15, line 38:

Change "filed concurrently of" to --filed concurrently on--

Signed and Sealed this

Fifteenth Day of June, 1993

Attest:

MICHAEL K. KIRK

Attesting Officer      Acting Commissioner of Patents and Trademarks